(12) United States Patent
Miller et al.

(10) Patent No.: US 7,452,207 B2
(45) Date of Patent: Nov. 18, 2008

(54) METHODS AND SYSTEMS FOR MODELING BITE REGISTRATION

(75) Inventors: Ross J. Miller, Sunnyvale, CA (US); Eric Kuo, Foster City, CA (US); Daniel E. Falvey, Tracy, CA (US); Andrew H. Trosien, Tracy, CA (US)

(73) Assignee: Align Technology, Inc., Santa Clara, CA (US)

( * ) Notice: Subject to any disclaimer, the term of this patent is extended or adjusted under 35 U.S.C. 154(b) by 631 days.

(21) Appl. No.: 11/115,271

(22) Filed: Apr. 25, 2005

(65) Prior Publication Data
US 2005/0196724 A1  Sep. 8, 2005

Related U.S. Application Data

(60) Continuation of application No. 10/424,370, filed on Apr. 24, 2003, now Pat. No. 6,948,936, which is a division of application No. 09/843,244, filed on Apr. 25, 2001, now Pat. No. 6,582,229.

(60) Provisional application No. 60/199,485, filed on Apr. 25, 2000.

(51) Int. Cl.
*A61C 11/00* (2006.01)
(52) U.S. Cl. ........................................... 433/71
(58) Field of Classification Search .............. 433/68, 433/69, 71, 213, 215
See application file for complete search history.

(56) References Cited

U.S. PATENT DOCUMENTS 696,774 A    4/1902  Tiffen et al.
730,658 A    6/1903  Huber
2,171,695 A  9/1939  Harper
2,845,708 A  8/1958  Gordan
3,916,526 A  11/1975 Schudy (Continued)

FOREIGN PATENT DOCUMENTS

EP    91876 A1    10/1983

(Continued)

OTHER PUBLICATIONS

Alexander et al., "The DigiGraph Work Station Part 2, Clinical Management," *JCO* (Jul. 1990), pp. 402-407.

(Continued)

*Primary Examiner*—Ralph A Lewis
(74) *Attorney, Agent, or Firm*—Townsend and Townsend and Crew LLP

(57) ABSTRACT

The present invention provides methods and devices for determining an axis of upper and lower jaw articulation of a patient and modeling jaw movement about such an axis, particularly with the use of computerized visual images. The methods comprise providing digital data sets of tooth and bite configuration information which may be used to determine an estimated condylar axis of rotation for a patient. A number of data sets may be acquired and utilized for such estimations. Data sets may be obtained with the use of bite registers. Such registers may be formed by a number of methods and device designs of the present invention. The resulting digital data sets and axis of articulation may then be utilized to generate animated visual images of a patient's jaws in various bite configurations throughout a given rotation around the determined axis. Accuracy of such dynamic imaging, in addition to the determination of the location of the condylar axis, may increase with the number of bite configurations recorded throughout the rotation.

9 Claims, 5 Drawing Sheets

U.S. PATENT DOCUMENTS

| | | |
|---|---|---|
| 3,950,851 A | 4/1976 | Bergersen |
| 4,003,132 A | 1/1977 | Beck |
| 4,014,096 A | 3/1977 | Dellinger |
| 4,195,046 A | 3/1980 | Kesling |
| 4,324,546 A | 4/1982 | Heitlinger et al. |
| 4,348,178 A | 9/1982 | Kurz |
| 4,478,580 A | 10/1984 | Barrut |
| 4,504,225 A | 3/1985 | Yoshii |
| 4,505,673 A | 3/1985 | Yoshii |
| 4,575,805 A | 3/1986 | Moermann et al. |
| 4,611,288 A | 9/1986 | Duret et al. |
| 4,656,860 A | 4/1987 | Orthuber et al. |
| 4,663,720 A | 5/1987 | Duret et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,837,732 A | 6/1989 | Brandestini et al. |
| 4,850,864 A | 7/1989 | Diamond |
| 4,856,991 A | 8/1989 | Breads et al. |
| 4,936,862 A | 6/1990 | Walker et al. |
| 4,937,928 A | 7/1990 | van der Zel |
| 4,964,770 A | 10/1990 | Steinbichler et al. |
| 4,975,052 A | 12/1990 | Spencer et al. |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,128,870 A | 7/1992 | Erdman et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,184,306 A | 2/1993 | Erdman et al. |
| 5,186,623 A | 2/1993 | Breads et al. |
| 5,257,203 A | 10/1993 | Riley et al. |
| 5,266,031 A | 11/1993 | Marigza |
| 5,273,429 A | 12/1993 | Rekow et al. |
| 5,278,756 A | 1/1994 | Lemchen et al. |
| 5,313,960 A | 5/1994 | Tomasi |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,503,552 A | 4/1996 | Diesso |
| 5,518,397 A | 5/1996 | Andreiko et al. |
| 5,533,895 A | 7/1996 | Andreiko et al. |
| 5,542,842 A | 8/1996 | Andreiko et al. |
| 5,549,476 A | 8/1996 | Stern |
| 5,587,912 A | 12/1996 | Andersson et al. |
| 5,605,459 A | 2/1997 | Kuroda et al. |
| 5,607,305 A | 3/1997 | Andersson et al. |
| 5,642,737 A | 7/1997 | Parks |
| 5,645,421 A | 7/1997 | Slootsky |
| 5,655,653 A | 8/1997 | Chester |
| 5,683,243 A | 11/1997 | Andreiko et al. |
| 5,733,126 A | 3/1998 | Andersson et al. |
| 5,740,267 A | 4/1998 | Echerer et al. |
| 5,829,441 A | 11/1998 | Kidd et al. |
| 5,879,158 A | 3/1999 | Doyle et al. |
| 5,905,658 A | 5/1999 | Baba |
| 5,975,893 A | 11/1999 | Chishti et al. |
| 6,089,868 A | 7/2000 | Jordan et al. |
| 6,152,731 A | 11/2000 | Jordan et al. |
| 6,582,229 B1 * | 6/2003 | Miller et al. ............ 433/213 |
| 6,948,936 B2 * | 9/2005 | Miller et al. ............ 433/214 |

FOREIGN PATENT DOCUMENTS

| | | |
|---|---|---|
| EP | 299490 A2 | 1/1989 |
| EP | 376873 A2 | 7/1990 |
| EP | 490848 A2 | 6/1992 |
| EP | 774933 B1 | 5/1997 |
| EP | 541500 A1 | 6/1998 |
| EP | 731673 B1 | 9/1998 |
| FR | 2369828 A1 | 6/1978 |
| FR | 2652256 A1 | 3/1991 |
| WO | WO 90/08512 A1 | 8/1990 |
| WO | WO 91/04713 A1 | 4/1991 |
| WO | WO 94/10935 A1 | 5/1994 |
| WO | WO 98/44865 A1 | 10/1998 |
| WO | WO 98/58596 A1 | 12/1998 |

OTHER PUBLICATIONS

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures, " IADR Abstracts, Program and Abstracts of Papers, 57th General Session, IADR Annual Session, Mar. 29, 1979-Apr. 1, 1979, New Orleans Marriot, *Journal of Dental Research*, vol. 58 ( Jan. 1979), Special Issue A, Abstract # 510, p. 221.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler, "3D Mapping of Maxillo-Facial Prosthesis," AADR Abstract #607,1980, 1 page total..

American Association for Dental Research, Summary of Activities, Mar. 20-23, 1980, Los Angeles. CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A Stereophotogrammetric System for the Detection of Prosthesis Loosening in Total Hip Arthroplasty", NATO Symposium on Applications of Human Biostereometrics, Jul. 9-13, 1978, SPIE vol. 166, pp. 112-123.

Baumrind et al., Mapping the Skull in 3-D, Reprinted from The Journal, *California Dental Association*, vol. 48, No. 2 (1972 Fall Issue) 11 pages total.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. pp. 142-166.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts. "*The Angle Orthodontist*, vol. 51 No. 3 (Jul. 1981), pp. 253-259.

Bernard et al., "Computerized Diagnosis in Orthodontics for Epidemiological Studies: A Progress Report", Abstracts of Papers, *Journal of Dental Research*; vol. 67, Special Issue Mar. 9-13, 1988, Abstract #449, p. 169.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized Analysis of Occlusion In The Postcanine Dentition," *American Journal of Orthodontics*, vol. 61, No. 3 (Mar. 1972), pp. 245-254.

Biggerstaff, "Computerized Diagnostic Setups and Sumulations," *The Angle Orthodontist*, vol. 40, No.1 (Jan. 1970), pp. 28-36.

Boyd et al., "Three Dimensional Diagnosis and Orthodontic Treatment of Complex Malocclusions Wlith the Invisalign Appliance", *Seminars in Orthodontics*, vol. 7, No. 4 (Dec. 2001), p. 274-293.

Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.

Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.

Burstone (interview), "Dr. Charles J. Burstone on The Uses of the Computer in Orthodontic Practice (Parts1 &2)," *Journal of Clinical Orthodontics*, (Part 1) vol. 8, No. 7, (Jul. 1979), pp. 443-453, (Part 2) vol. 8, No. 8, (Aug. 1979) pp. 539-551.

Burstone et al., "Precision Adjustment of the Transpalatal Lingual Arch: Computer Arch Form Predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research*, No. 201 (December 1985), pp. 60-67.

Chiappone, "Constructing the Gnathologic Setup And Positioner" *J. Clin. Orthod.*, 14:121-133, 1980.

Cottingham, "Gnathologic Clear Plastic Positioner" *Am. J. Orthod.*, Vol. 55, No. 1, (Jan. 1969), pp. 23-31.

Crawford, "Computers in Dentistry: Part 1: CAD/CAM: The Computer Moves Chairside," "Part 2: F. Duret—A Man With A Vision," "Part 3: The Computer Gives New Vision- Literally," "Part 4: Bytes 'N Bites" The Computer Moves From The Front Desk To The Operatory, *Canadian Dental Journal*, vol. 54(9), , (1988), pp. 661-666.

Crawford, "CAD/CAM in the Dental Offics: Does It Work?" *Canadian Dental Journal*, vol. 57, No. 2 ( Feb. 1991), pp. 121-123.

Crooks, "CAD/CAM Comes to USC," *USC Dentistry*, (Spring 1990) pp. 14-17.

Cureton, "Correcting Malaligned Mandibular Incisors With Removable Retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM 'DCS Titan System' for Production of Crowns/Bridges" *DCS Production AG*, Jan. 1992, pp. 1-7.

Defranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 2 pages total.

Duret et al, "CAD-CAM in Dentistry," *Journal of the American Dental Association*, vol. 117 (Nov. 1988), pp. 715-720.

Duret et al., "CAD/CAM Imaging in Dentistry," *Current Opinion in Dentistry*, vol. 1 (1991), pp. 150-154.

Duret, "Vers une prosthese informatisee, " (English translation also attached), *Tonus*, vol. 75, (Nov. 15, 1985), pp. 55-57.

Duret, "The Dental CAD/CAM, General Description of the Project," *Hennson International Product Brochure*, Jan. 1986., 18 pages total.

Economides, "The Microcomputer in the Orthodontic Office," *JCO*, (Nov. 1979), pp. 767-772.

Elsasser, "Some Observations on the History and Uses of the Kesling Positioner" *Am. J. Orthod.*, Vol. 36, No. 5, (May 1950) pp. 368-374.

Faber et al., "Computerized interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., "Accuracy of Cephalometric Prediction in Orthognathic Surgery, " Abstract of Papers, *Journal of Dental Research*, vol. 70 (1987), pp. 754-760.

Grayson, "New Methods for Three Dimensional Analysis of Craniofacial Deformity," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5-6.

Guess et al., "Computer Treatment Estimates in Orthodontics and Orthognathic Surgery," *JCO*, (Apr. 1989), pp. 262-228.

Heaven et al., "Computer-based Image Analysis of Artificial Root Surface Caries," Abstracts of Papers, *Journal of Dental Research*, vol. 70, Apr. 17-21, 1991, #2094, p. 528.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

JCO Interviews, "Craig Andreiko , DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The Problem, Electronic Data Transmission and the Law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case Reports on Tooth Positioners Using LTV Vinyl Silicone Rubber" J. Nihon University School of Dentistry, 26(1):11-29, 1984.

Kamada et al., "Construction of Tooth Positioners With LTV Vinyl Silicone Rubber and Some Case Reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res.* , vol. 63, No. 11 (Nov. 1984), pp. 1298-1301.

Kesling. "Coordinating the Predetermined Pattern and Tooth Positioner With Conventional Treatment" *Am. J. Orthod. Oral. Surg.*, 32:285-293, 1946.

Kesling, "The Philosophy of the Tooth Positioning Appliance" *Am. J. Orthod. Oral. Surg.*, 31(6):297-304, 1945.

Kleemann et al., "The Speed Positioner" *J. Clin. Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal of The American Dental Assoc.*, vol. 118, No. 6 (Jun. 1989), pp. 703-707.

Manetti et al., "Computer-aided Cefalometry and New Mechanics in Orthodontics" (Article Summary in English, article in German), *Fortschr. Kieferorthop.* 44, 370-376 (No. 5), 1983.

McCann. Inside the ADA, *Journal Of The American Dental Assoc.*, vol. 118 (Mar. 1989) pp. 286-294.

McNamara et al., "Invisible Retainers", *J. Clinical Orthodontics*, (Aug. 1985) pp. 570-578.

McNamara et al., Chapter 19: Invisible Retainers, *Orthodontic and Orthopedic Treatment in the Mixed Dentition*, Needham Press, Jan. 1993. pp. 347-353.

Moermann et al., "Computer Machined Adhesive Porcelain Inlays: Margin Adaptation after Fatigue Stress," IADR Abstract 339, *Journal of Dental Research*, vol. 66(a) (1987), p. 763.

Mörmann et al., "Marginal Adaptation von adhasiven Porzellaninlays in vitro, "*Schwizerische Monatsshrift fur Zahnmedizin*, vol. 85 (1985), p. 1118-1129.

Nahoum, "The Vacuum Formed Dental Contour Appliance" *The New York State Dental Journal*, 30(9):385-390, Nov. 1964.

Nash, "CEREC CAD/CAM Inlays: Aesthetics and Durability in a Single Appointment," *Dentistry Today*, (Oct, 1990), pp, 20,22-23,54.

Nishiyama et al., "A New Construction of Tooth Repositioner By LTV Vinyl Silicone Rubber" J. Nihon University School of Dentistry, 19(2):93-102, 1977.

Pinkham, "Foolish' Concept Propels Technology," *Dentist*, Jan./Feb. 1989, 3 pages total.

Pinkham, "Inventor's CAD/CAM may transform dentistry," *Dentist*, Sep. 1990, 3 pages total.

Ponitz,"Invisible Retainers", *Am. J. Orthodontics*, vol. 59, No. 3, Mar. 1971, pp. 266-272.

Procera Research Projects, *Procera Research Projects* 1993—Abstract Collection, 1993, pp. 3-24.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, "Feasibility of an Automated System for Production of " Dental Restorations, PhD Thesis, Univ. of Minnesota, Nov. 1988, 244 pages total.

Richmond et al., Research Reports, "The Development of a 3D Cast Analysis System," *British Journal of Orthodontics*, vol. 13, No. 1, (Jan. 1986) pp. 53-54.

Richmond, "Recording The Dental Cast In Three Dimensions," *Am. J. Orthod. Dentofac. Orthop.*, vol. 92, No. 3, (Sep. 1987), pp. 199-206.

Rudge, "Dental arch analysis: arch form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (March 1992), pp. 210-220.

Schellhas et al., "Three-Dimensional Computed Tomography in Maxillofacial Surgical Planning," *Arch Otolamgol Head Neck Surg.* vol. 114 (Apr. 1988), pp. 438-442.

Shilliday, "Minimizing finishing problems with the mini-positioner" *Am. J. Orthod.* 59:596-599, 1971.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), Dtsch Zahnärztl Z 45, 314-322, 1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050342, filed on Jun. 20, 1997, 41 pages total.

Van Der Linden et al., "Three-Dimensional Analysis of Dental Casts by Means of the Optocom," *J Dent Res*, Jul.-Aug. 1972, vol. 51, No. 4, p. 1100.

Van Der Linden, "A New Method to Determine Tooth Positions and Dental Arch Dimensions,"Jul.-Aug. 1972, p. 1104.

Van Der Zel, "Ceramic-fused-to-metal Restorations with a New CAD/CAM System," *Quintessence International*, vol. 24(11) (1993), pp. 769-778.

Varady et al., Reverse engineering of geometric models—an introduction. Computer-Aided Design, 29 (4):255-268, 1997.

Warunek et al., "Clinical use of silicone elastomer appliances" *JCO*, MH (10):694-700, 1989.

Warunek et al., "Physical And Mechanical Properties of Elastomers in Orthodontic Positioners" *Am. J. Orthod. Dentofac. Orthop.*, 95:388-400, 1989.

Wells, "Application of the Positioner Appliance in Orthodontic Treatment" *Am. J. Orthodont.*, 58:351-366, 1970.

Williams, "Dentistry and CAD/CAM: Another French Revolution,"*Journal of Dental Practice Admin.*, (Jan./Mar. 1987), pp. 2-5.

Williams, "The Switzerland and Minnesota Developments in CAD/CAM," *Journal of Dental Practice Admin.*, (Apr./Jun. 1987). pp. 50-55.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, (Aug. 1990), p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, (1990), pp. 2051-2053.

Yamamoto et al., "Optical Measurement of Dental Cast Profile and Application to Analysis of Three-Dimensional Tooth Movement in Orthodontics," *Frontiers in Med. and Biol. Eng'g*, vol. 1, No. 2 (1988), pp. 119-130.

* cited by examiner

METHODS AND SYSTEMS FOR MODELING BITE REGISTRATION

CROSS-REFERENCES TO RELATED APPLICATIONS

The present application is a continuation of U.S. patent application Ser. No. 10/424,370, filed Apr. 24, 2003, which is a divisional of U.S. patent application Ser. No. 09/843,244, filed Apr. 25, 2001, and now issued as U.S. Pat. No. 6,582,229, which claimed benefit of provisional Application No. 60/199,485, filed on Apr. 25, 2000, the full disclosures of which are incorporated herein by reference.

SUMMARY OF THE INVENTION

The present invention provides methods and devices for determining an axis of upper and lower jaw articulation of a patient and modeling jaw movement about such an axis, particularly with the use of computerized visual images. The methods comprise providing digital data sets of tooth and bite configuration information which may be used to determine an estimated condylar axis of rotation for a patient. A number of data sets may be acquired and utilized for such estimations. In a preferred embodiment, data sets representing the upper jaw, lower jaw and at least two bite registers may be used to determine an axis of rotation. In an additional embodiment, data sets representing at least a first and a second bite configuration may be used to determine such an axis of rotation. Such bite configurations may be guided with the use of bite registers. The above mentioned bite registers may be formed by a number of methods and device designs of the present invention. The resulting digital data sets and axis of articulation may then be utilized to generate animated visual images of a patient's jaws in various bite configurations throughout a given rotation around the determined axis. Accuracy of such dynamic imaging, in addition to the determination of the location of the condylar axis, may increase with the number of bite configurations recorded throughout the rotation.

In a first aspect of the methods of the present invention, digital data sets representing the upper jaw of a patient, the lower jaw of the patient and at least two bite registers may be used to determine an axis of rotation or articulation for the patient's jaws. Digital data sets representing an object may be provided by scanning the object or a three-dimensional model of the object. The jaws of the patient may be modeled by producing a plaster cast of the patient's teeth. After the tooth cast is obtained, it may be digitally scanned using a conventional laser scanner or other range acquisition system to produce the digital data set. A bite register may be similarly scanned to obtain a bite digital data set representing the register.

In a second aspect of the methods of the present invention, a bite register may be formed by a number of methods using a variety of bite registration devices. Bite registers may record the shape, location and orientation of the teeth of the upper jaw in relation to the teeth of the lower jaw when the jaws are in a given bite configuration. In general, it is only necessary to record the features and orientations of an adequate number of teeth to determine the orientations of the remaining teeth. Thus, bite registers are typically structures having an impression of at least a surface of a tooth in the upper jaw and a surface of a tooth in the lower jaw when the upper and lower jaws are in a predetermined bite position.

In a first embodiment, a bite register may be produced by biting a structure comprised of malleable material between the occlusional surfaces of the posterior teeth. In this case, the structure may be a block of such material having a predetermined thickness. When placed on both sides of the mouth between the posterior teeth, as described, the patient may then bite down on the blocks to record the bite configuration. Since the blocks are comprised of a malleable material, such as wax, polyvinyl silaxane, acrylic, plastic, plaster or any other suitable impression material, the teeth and associated dental features, such as gingiva, will imprint in the blocks. It may be appreciated that one continuous block may be used rather than two separate blocks, one on each side of the mouth, or any other shape and/or number of such blocks to effectively form an impression of the occlusional surfaces.

The above described methodology of forming a bite register records a bite configuration at one point in rotation of the jaws around the condylar axis. Starting from a closed position, the lower jaw rotates around the condylar axis as the bite opens to a fully opened position. A bite configuration may be registered or recorded at an point in this rotation. The point in rotation may be preselected by the thickness of the block prior to impression in the above described example. The thicker the block, the more open the bite. Thus, a series of bite registers may be formed with blocks of increasing thickness to model the bite configurations throughout the rotation or throughout a specific range of the rotation. Such a series may be comprised of two, three, four, five, or more of such bite registers, each of which may be scanned to provide a series of bite digital data sets.

In a second embodiment, a bite register may be produced by pressing a structure comprised of malleable material against the facial surfaces of the anterior teeth. It has been determined that the orientations or spatial relationships of the anterior teeth of the upper and lower jaws may adequately determine the orientations of the remaining teeth in a given bite configuration. Such a structure may be comprised of the malleable material itself, or it may be supported by a holder. The holder may be comprised of a plate, contoured to generally fit a dental arch curve, and a handle. The plate may support a malleable material, such as that described previously, and may be pressed against the facial surfaces of the anterior teeth.

Alternatively, in a third embodiment, the holder may be comprised of an upper portion and a lower portion joined by a separator to orient the upper and lower jaws in a predetermined bite position. Malleable material may be mounted on the upper and lower portions of the holder to form registration surfaces. An upper registration surface may contact a surface of a tooth in an upper jaw of a patient and a lower registration surface may contact a surface of a tooth in a lower jaw of a patient. Simultaneous contact of these registration surfaces against the appropriate teeth, by, for example, biting the registration device, may record bite information correlated to the predetermined orientation of the registration surfaces. Such orientation may be fixed or it may be adjustable to join the upper and lower registration surfaces in a series of predetermined orientations. In either case, the bite information may comprise the shape, location and orientation of at least one tooth surface in the upper jaw of a patient in relation to at least one tooth surface in the lower jaw of the patient.

Again, the above described methodology of forming a bite register records a bite configuration at one point in rotation of the jaws around the condylar axis. A bite configuration may be registered or recorded at any point in this rotation. The point in rotation may be preselected by opening the jaws to a desired configuration by any means. In the case of bite registration devices comprising a separator, the registration surfaces may be separated and oriented to open the jaws to a desired configuration based on the characteristics of the separator. The separator may join the upper and lower registration surfaces in a fixed predetermined orientation, or the separator may be adjustable to join the registration surfaces in a series of orientations. In any case, a series of bite registers may be formed to model the bite configurations throughout the rotation or throughout a specific range of the rotation. Such a series may be comprised of two, three, four, five, or more of such bite registers, each of which may be scanned to provide a series of bite digital data sets.

In a third aspect of the methods of the present invention, determination of an axis of upper and lower jaw articulation of a patient and modeling of jaw movement about such an axis may be achieved, particularly with the use of computerized visual images.

In a fourth aspect of the methods of the present invention, digital data sets representing a first bite configuration and a second bite configuration may be used to determine an axis of rotation or articulation for the patient's jaws. This is similar to the first aspect of the methods of the present invention, described above, but utilizes different data sets to determine an axis of rotation. Rather than scanning the upper jaw, lower jaw and bite registrations separately to obtain individual representative digital data sets, the components may be assembled in a bite configuration and scanned together. For example, a plaster cast of the lower jaw may be positioned with the teeth facing upwards. A bite register may then be placed on the cast of the lower jaw, and a plaster cast of the upper jaw may be placed over the cast of the lower jaw with the teeth downwards, guided by and resting on the bite register. In this manner, the plaster casts of a patient's upper and lower dentition to be placed relative to one another in a given bite configuration. A cylindrical scan may then acquired for the lower and upper casts in their relative positions. The scanned data provides a digital model representing an object which is the combination of the patient's arches positioned in a first bite configuration. This may be repeated for a second bite configuration. The second bite configuration may be any desired bite configuration which is different from the first bite configuration. To accomplish this, a new bite register may be obtained from the patient in the second bite configuration. Casts of the teeth may be assembled and scanned as described above.

Once digital data sets are acquired, by any method, an image can be presented and manipulated on a suitable computer system equipped with computer-aided design software. The image manipulation may comprise rotating an image of the lower jaw around the determined axis of articulation to model the movement of a patient's jaws. Such movement may range between a closed position and a fully open position or a portion of the range therein. The computer system may be provided with rules and algorithms which move the jaw(s) in a fully automatic manner, i.e. without user intervention. Such rules and algorithms may be based on the digital data sets representing the differing bite configuration and the determined axis of articulation.

Although a few known bite configurations may be represented, it may be desired to interpolate intermediate bite configurations between the known configurations to visually portray a range of jaw movement. Usually, the successive digital data sets representing these intermediate bite configurations are produced by determining positional differences between selected individual teeth in a digital data set of a first bite configuration and digital data set of a second bite configuration and interpolating said differences. Such interpolation may be performed over as many discrete stages as may be desired, usually at least three, often at least four, more often at least ten, sometimes at least twenty-five, and occasionally forty or more. Many times, the interpolation will be linear interpolation for some or all of the positional differences. Alternatively, the interpolation may be non-linear.

Often, the user will specify certain target intermediate bite configurations, referred to as "key frames," which are incorporated directly into the intermediate digital data sets. The methods of the present invention then determine successive digital data sets between the key frames in the manner described above, e.g. by linear or non-linear interpolation between the key frames. The key frames may be determined by a user, e.g. the individual manipulating a visual image at the computer used for generating the digital data sets.

DESCRIPTION OF THE SPECIFIC EMBODIMENTS

Bite configurations may be recorded with the use of a bite register. A bite register is a device which records the shape, location, and orientation of the teeth of the upper jaw in relation to the teeth of the lower jaw when the jaws are in a given bite configuration. These relationships may then be used to recreate the bite configuration with mechanical models or computerized images of the teeth. If a series of bite configurations are recorded, for example from a closed bite configuration to a fully open bite configuration, the full rotation of the condylar axis may be modeled for a given patient. Accuracy of the dynamic modeling, in addition to the determination of the location of the condylar axis, may increase with the number of bite configurations recorded throughout the rotation.

Figure 1A:
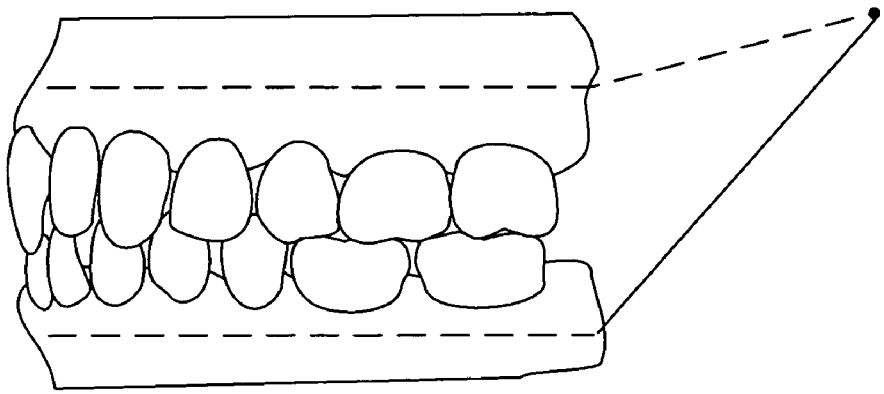
FIGS. 1A-1C show various bite configurations of a patient illustrating the orientations of the upper and lower jaws in rotation about the condylar axis.
Figure 1B:
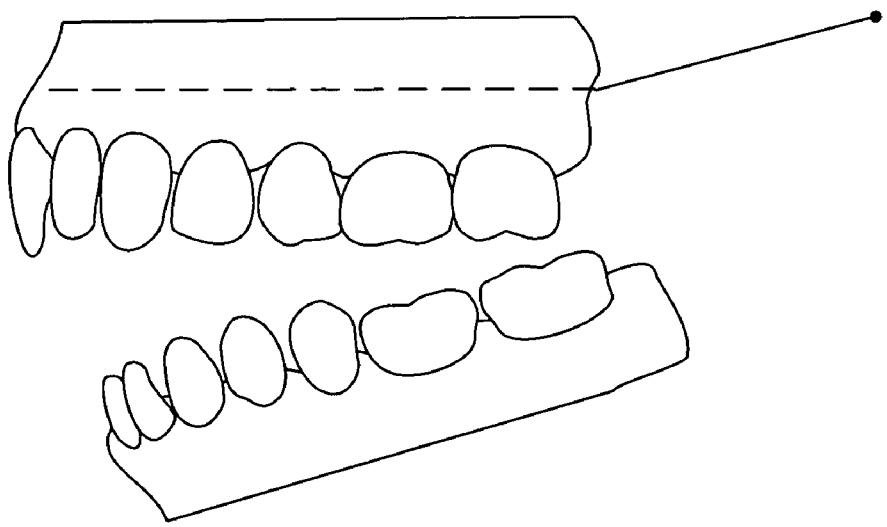
Figure 1C:
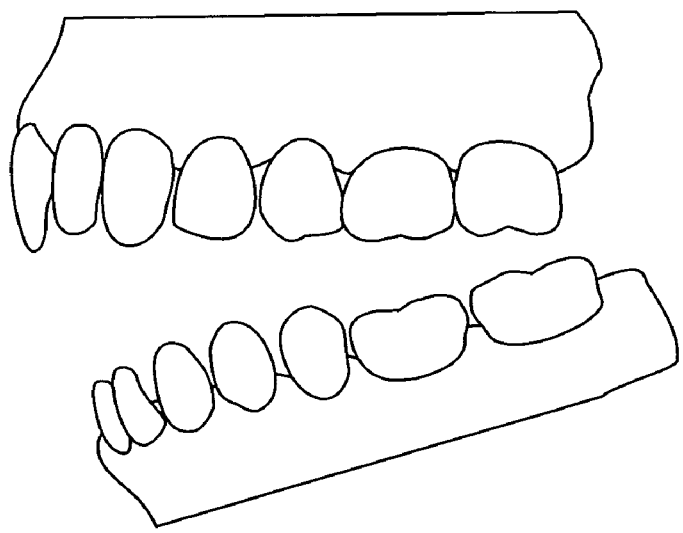
Figure 2:
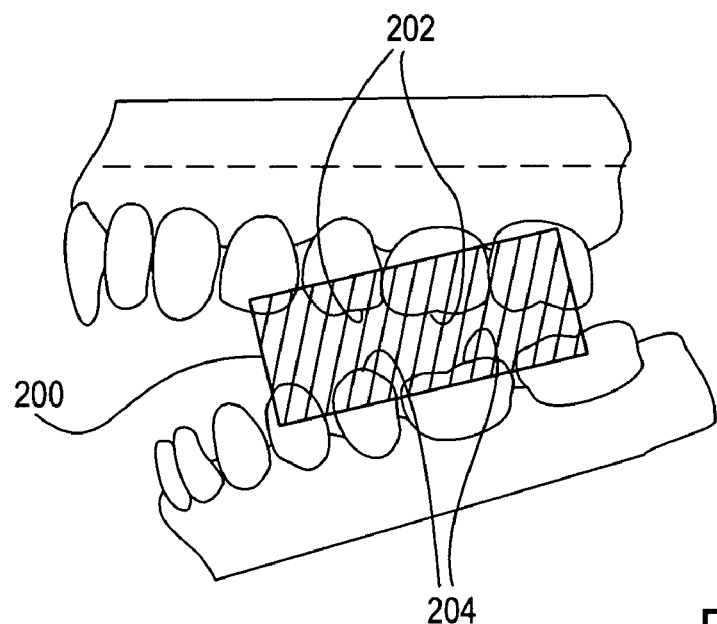
FIG. 2 is a side view of a the upper and lower jaws of a patient registering a bite in a block of malleable material placed between the occlusional surfaces of the posterior teeth.

A number of methodologies may be used to record bite configurations to form a bite register. In general, bite registers record the features and orientations of an adequate number of teeth to determine the orientations of the remaining teeth. This is typically achieved by forming impressions of the teeth of both the upper and lower jaws when the jaws are in a biting configuration. Referring to FIG. 2, this may be achieved by placing a block 200 of malleable material between the occlusional surfaces of the upper and lower posterior teeth 202, 204 of a patient as shown. Typically, two such blocks 200 may be used, one placed on the right side of the mouth and one in the same or similar position on the left side. Thus, when the patient bites down on the blocks 200, the bite configuration on both sides of the mouth may be recorded simultaneously.

Figure 3:
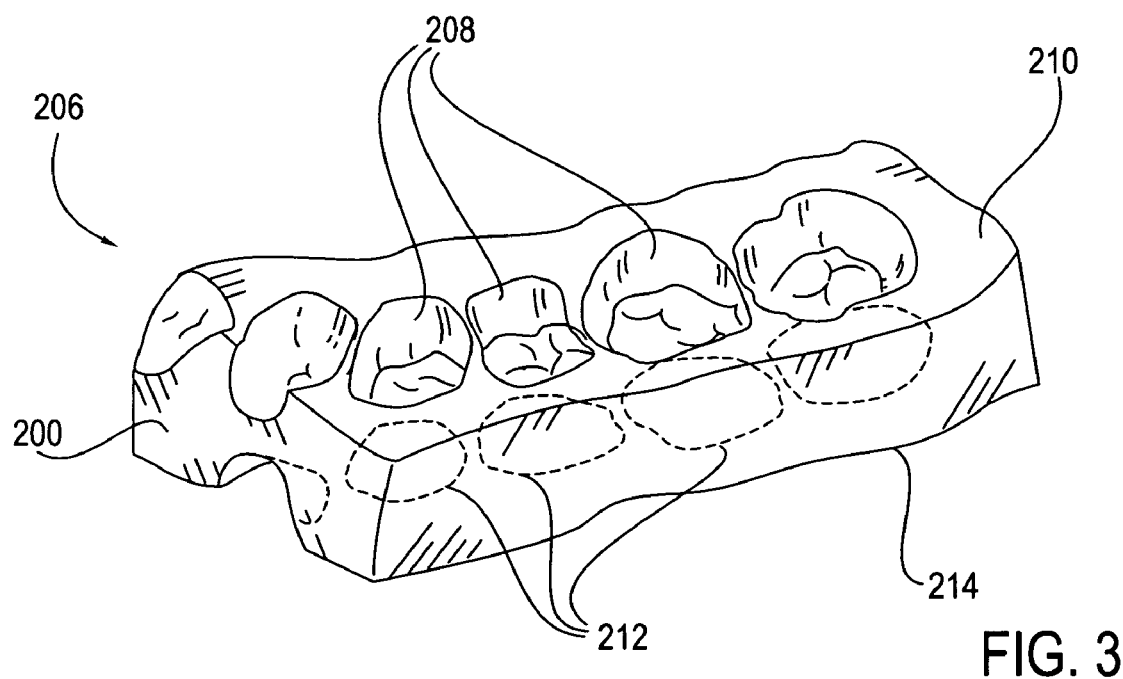
FIG. 3 is a perspective view of a bite register resulting from the formation illustrated in FIG. 2.

Since the block 200 is comprised of a malleable material, such as wax, polyvinyl silaxane, acrylic, plastic, plaster or any suitable impression material, the teeth 202, 204 will imprint or form depressions in the block 200 corresponding to the shapes, locations and orientations of the teeth 202, 204. The result, as shown in FIG. 3, is a bite register 206. Here, impressions 208 of the surfaces of the teeth and associated dental features, such as gingiva, in the top jaw may be seen in the top surface 210 of the block 200. Similarly, impressions 212 of the surfaces of the teeth and associated dental features in the bottom jaw may be made in the bottom surface 214 of the block 200, represented by dashed lines. Thus, spatial relationships between the upper jaw and the lower jaw may be recorded.

The above described methodology of forming a bite register records a bite configuration at one point in rotation of the jaws around the condylar axis. Starting from a closed position, the lower jaw rotates around the condylar axis as the bite opens to a fully opened position. A bite configuration may be registered or recorded at any point in this rotation. The point in rotation may be preselected by the thickness of the block prior to impression in the above described example. The thicker the block, the more open the bite. Thus, a series of bite registers may be formed with blocks of increasing thickness to model the bite configurations throughout the rotation or throughout a specific range of the rotation.

In a preferred embodiment of a method of the present invention, a bite register may be comprised of an impression of the facial surfaces of the anterior teeth. It has been determined that the orientations or spatial relationships of the anterior teeth of the upper and lower jaws may adequately determine the orientations of the remaining teeth in a given bite configuration. In particular, the spatial relationships between the facial surfaces of the incisors may be adequate to model a bite configuration. Using these surfaces to form a bite register provide a number of advantages: 1) the facial surfaces of the anterior teeth are easily accessible for impression formation since the surfaces lie against the lips, 2) the surfaces required for adequate modeling of the bite configuration may be relatively low, typically requiring only the anterior surfaces of the incisors, possibly only requiring one surface on the top jaw and a correlating surface on the bottom jaw, and 3) variability in the point in the condylar axis rotation chosen for a given bite configuration may be reduced since the jaws may be opened to a given point in the rotation by non-malleable supports. In the previously described method, the jaws were set to a given point in the rotation by the thickness of a block of malleable material placed between the jaws. However, the act of biting the blocks may compress the blocks to an undetermined thickness, increasing the variation in actual axis rotation. In the above described embodiment of a method of the present invention, the jaws may be set to a given point in the rotation by any means, such as shim stock or non-malleable supports placed between the jaws. The bite may then be registered by forming an impression of the facial surfaces of the anterior teeth as described.

Figure 4:
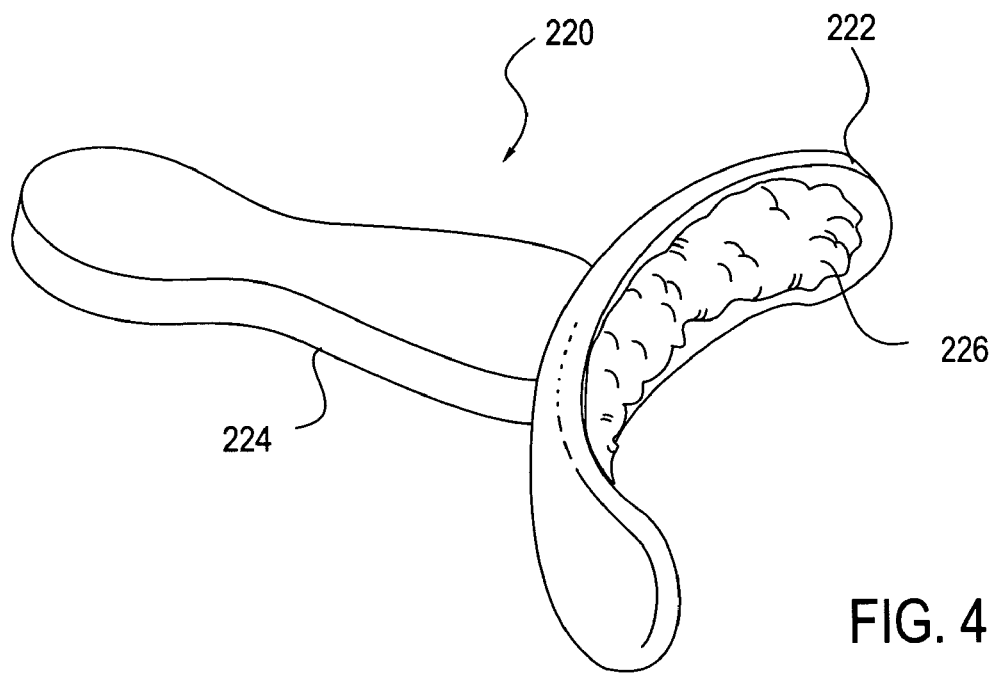
FIG. 4 is a illustration of a bite registration device.
Figure 5:
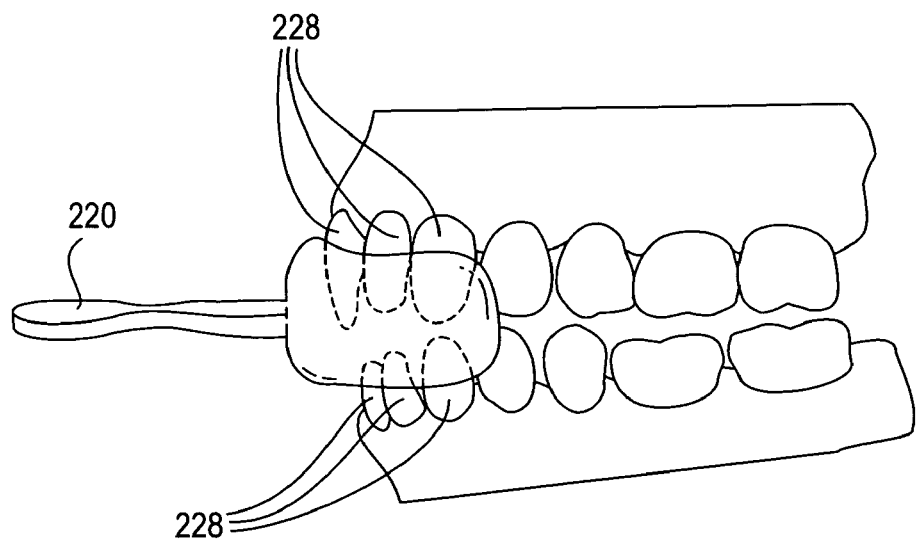
FIG. 5 illustrates a bite registration device, as shown in FIG. 4, in use to form a bite register.

Referring to FIG. 4, such an impression may be made with the use of a holder 220. Such a holder 220 may be comprised of a plate 222, contoured to generally fit a dental arch curve, and a handle 224. The plate 222 may support a malleable material 226, such as wax, polyvinyl silaxane, acrylic, plastic, plaster or any suitable impression material, into which an impression may be made. As shown in FIG. 5, the material (not shown) and holder 220 may be pressed against the facial surfaces of the anterior teeth 228. In this manner, the material 226 may contact the facial tooth surfaces and press through any space between the teeth of the upper and lower jaws.

Figure 6:
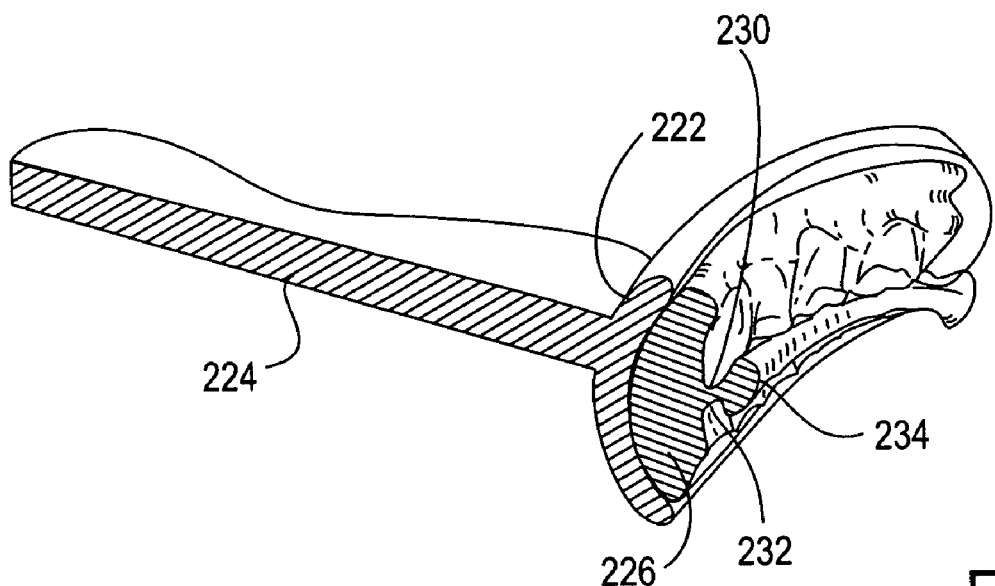
FIG. 6 illustrates a bite register formed by a method as shown in FIG. 5.

Thus, the material may also contact some occlusional and lingual surfaces of the teeth 228. This is particularly the case when the bite is at least partially open. The resulting bite registration may appear as in FIG. 6. Here, a cross-section of the material 226, plate 222 and handle 224 are shown to illustrate typical contours of the impression in the malleable material 226. An upper depression 230 may reflect the surfaces of an incisor in the upper jaw and a lower depression 232 may reflect the surfaces of an incisor in the lower jaw. A protrusion 234 may be formed between these depressions 230, 232 due to the material 226 pressing between the jaws. Similar impressions or depressions from the surfaces of the surrounding teeth may be seen in perspective view in FIG. 6.

It may be appreciated that the curvature of the plate may serve to provide improved contact of the malleable material with the facial tooth surfaces. However, the plate may have any contour to achieve desired results. Also, the malleable material may be used without the holder or similar device. In such a case, the material itself may simply be pressed against the teeth.

Figure 7:
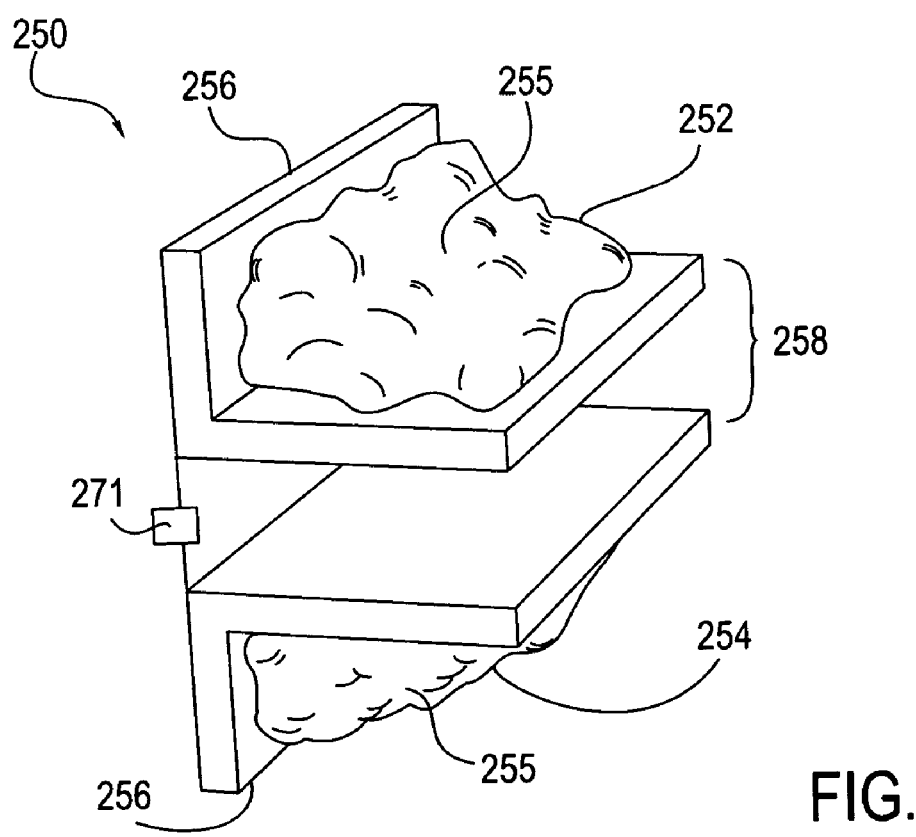
FIG. 7 is a perspective view of a bite registration device having an adjustable separation between bite registration surfaces.
Figure 8:
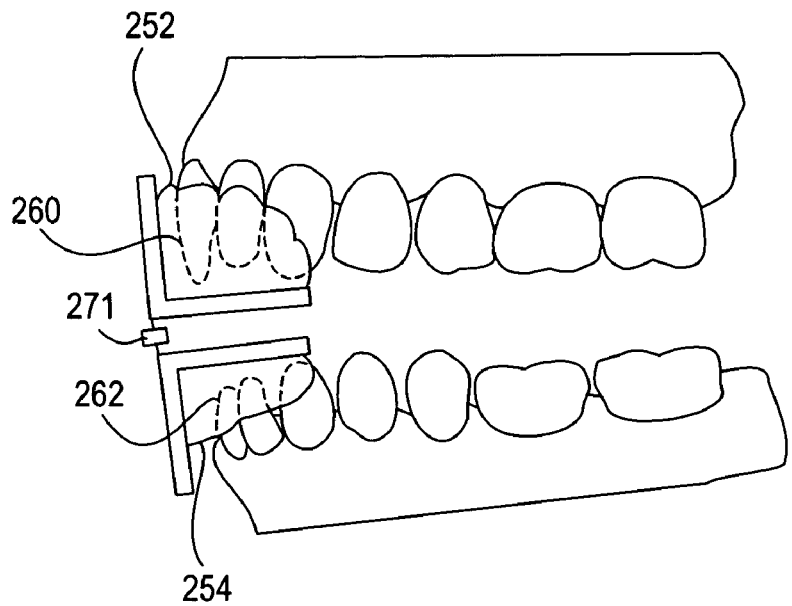
FIG. 8 illustrates a bite registration device, as shown in FIG. 7, in use to form a bite register.

Referring to FIG. 7, a preferred embodiment of a bite registration device 250 to form an impression of the facial surfaces of the anterior teeth is depicted. Such a device 250 may be comprised of an upper registration surface 252, a lower registration surface 254 and a separator 255 joining the upper and lower registration surfaces 252, 254. In this example, each registration surface is comprised of malleable material 255 supported by a holder 256. The holders 256 are attached to the separator 255 which holds the registration surfaces 252, 254 apart at a desired distance 258. In this example, the separator 255 is adjustable so that the distance 258 between the registration surfaces 252, 254 may be set to a desired amount of separation. It may also be possible for the separator 255 to adjust the orientation of the registration surfaces 252, 254, such as varying the tilt of the surfaces and/or the spatial relationship between the two surfaces. To form a bite register, as illustrated in FIG. 8, a patient may bite the bite registration device 250 so that a surface of a tooth in the upper jaw 260 contacts the upper registration surface 252 and a surface of a tooth in the lower jaw 262 contacts the lower registration surface 254. Such contact forms an impression of the tooth surfaces 260, 262 in the registration surfaces 252, 254, thus recording the bite configuration. When biting the registration device 250, the predetermined orientations of the registration surfaces 252, 254 may set the jaws to a given point in rotation about the condylar axis. Thus, the further apart the registration surfaces 252, 254 are set, the more open the bite configuration becomes. This may ensure the recording of a bite configuration at a specific point in rotation about the condylar axis, and it may reduce variability in such recording. To record bite configurations throughout a portion of the range of rotation, a number of bite registers may be made with the registration surfaces at differing separation distances.

Figure 9:
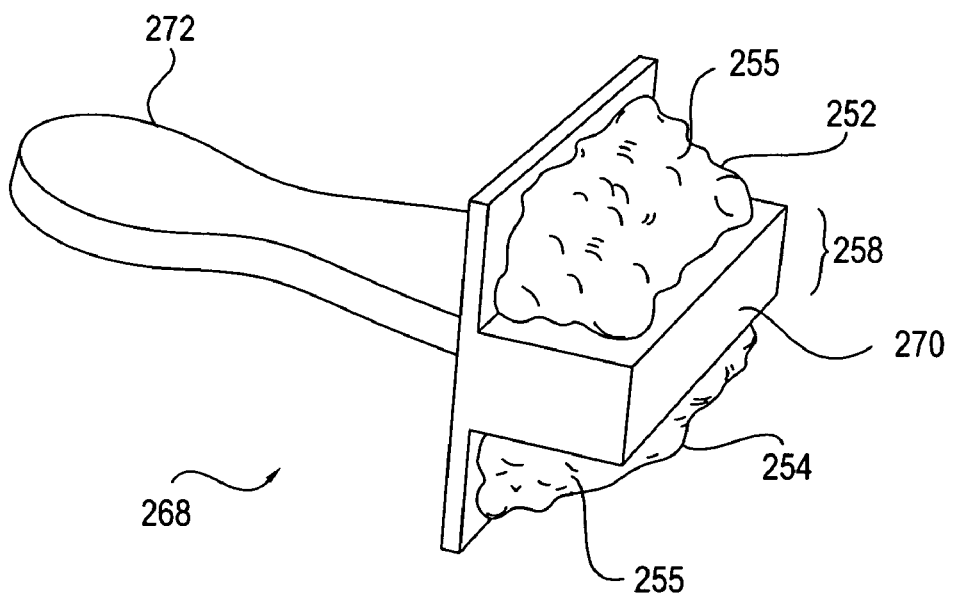
FIG. 9 is a perspective view of a bite registration device having a fixed separation between bite registration surfaces.

This may easily be achieved with an adjustable registration device, as described above. However, this may also be achieved with the use of a number of registration devices, each with a fixed separation distance. Such a device embodiment is depicted in FIG. 9. Here, the registration surfaces 252, 254 are comprised of a malleable material 255 supported by a separator 270, which is attached to a handle 272. The separator 270 may be a solid structure which holds the material 255 apart at a desired distance 258. The structure may also provide a desired orientation of the registration surfaces 252, 254, providing a specific tilt of the surfaces and/or a spatial relationship between the two surfaces. To form a bite register, a patient may bite the bite registration device 268 so that a surface of a tooth in the upper jaw 260 contacts the upper registration surface 252 and a surface of a tooth in the lower jaw 262 contacts the lower registration surface 254, as previously depicted in FIG. 8. Again, such contact forms an impression of the tooth surfaces 260, 262 in the registration surfaces 252, 254, thus recording the bite configuration. When biting the registration device 268, the predetermined orientations of the registration surfaces 252, 254 may set the jaws to a given point in rotation about the condylar axis. To record bite configurations throughout a portion of the range of rotation, a number of bite registers may be made with the registration surfaces at differing separation distances.

Bite registers obtained from any method may be used to recreate the bite configuration of a patient with mechanical models or computerized images of the teeth. As previously mentioned, a series of bite registers may be used to model the bite configurations throughout a range of rotation about the condylar axis. A series of such models may then be used to determine the location of the condylar axis.

The present invention provides a method for determining an axis of upper and lower jaw articulation. A preferred embodiment of a method of the present invention utilizes an upper digital data set, representing the upper jaw of the patient, a lower digital data set, representing the lower jaw of the patient, and at least two bite digital data sets, each representing a bite register. However, three or more digital data sets may also be used.

Digital data sets of information to model an object, such as a patient's upper jaw, a patient's lower jaw or a bite register, may be obtained in a variety of ways. For example, the object may be scanned or imaged using well known technology, such as X-rays, three-dimensional X-rays, computer-aided tomographic images or data sets, magnetic resonance images, etc. Methods for digitizing such conventional images to produce data sets useful in the present invention are well known and described in the patent and medical literature. However, digital data sets of a patient's teeth will typically rely on first obtaining a plaster cast of the patient's teeth by well known techniques, such as those described in Graber, Orthodontics: Principle and Practice, Second Edition, Saunders, Philadelphia, 1969, pp. 401-415. After the tooth casting is obtained, it can be digitally scanned using a conventional laser scanner or other range acquisition system to produce the digital data set. The data set produced by the range acquisition system may, of course, be converted to other formats to be compatible with other software. General techniques for producing plaster casts of teeth and generating digital models using laser scanning techniques are described, for example, in U.S. Pat. No. 5,605,459, the full disclosure of which is incorporated herein by reference.

There are a variety of range acquisition systems, generally categorized by whether the process of acquisition requires contact with the three dimensional object. A contact-type range acquisition system utilizes a probe, having multiple degrees of translational and/or rotational freedom. By recording the physical displacement of the probe as it is drawn across the sample surface, a computer-readable representation of the sample object is made. A non-contact-type range acquisition device can be either a reflective-type or transmissive-type system. There are a variety of reflective systems in use. Some of these reflective systems utilize non-optical incident energy sources such as microwave radar or sonar. Others utilize optical energy. Those non-contact-type systems working by reflected optical energy further contain special instrumentation configured to permit certain measuring techniques to be performed (e.g., imaging radar, triangulation and interferometry).

A preferred range acquisition system is an optical, reflective, non-contact-type scanner. Non-contact-type scanners are preferred because they are inherently nondestructive (i.e., do not damage the sample object), are generally characterized by a higher capture resolution and scan a sample in a relatively short period of time. One such scanner is the Cyberware Model 15 manufactured by Cyberware, Inc., Monterey, Calif.

The methods of the present invention will rely on manipulating the data sets at a computer or workstation having a suitable graphical user interface (GUI) and software appropriate for viewing and modifying the generated images. Specific aspects of the software will be described in detail hereinafter.

According to the methods of the present invention, the axis of upper and lower jaw articulation may also be determined by manipulating data sets of bite configurations. A preferred embodiment of such a method will be described. To begin, a bite register is obtained from a patient in a first bite configuration. This may be any desired bite configuration ranging from closed to fully open. The bite register enables mechanical tooth/jaw models, such as plaster casts, to be positioned in a representative bite configuration for scanning. This is usually accomplished by first placing the lower cast in front of the scanner, with the teeth facing upwards, then placing the bite register on top of the lower cast, and finally by placing the upper cast on top of the lower cast, with the teeth downwards, resting on the bite register. A cylindrical scan is then acquired for the lower and upper casts in their relative positions. The scanned data provides a digital model of medium resolution representing an object which is the combination of the patient's arches positioned in the first bite configuration. This may be repeated for a second bite configuration. The second bite configuration may be any desired bite configuration which is different from the first bite configuration. To accomplish this, a new bite register may be obtained from the patient in the second bite configuration. Casts of the teeth may be assembled and scanned as described above.

What is claimed is:

1. A method for digitally modeling a bite configuration of a patient, the method comprising:
   acquiring a first digital scan of at least some of a patient's upper and lower teeth while the patient is biting a registration device oriented at a first separation distance;
   acquiring at least a second digital scan of at least some of the patient's upper and lower teeth while the patient is biting a registration device oriented at a second separation distance;
   generating at least first and second bite digital data sets from the first and second digital scans; and
   locating a condylar axis of the patient, based on at least the first and second digital scans and the first and second bite digital data sets.

2. A method as in claim 1, further comprising:
   acquiring a third digital scan of at least some of the patient's teeth while the patient is biting a registration device oriented at a third separation distance; and
   generating a third bite digital data set from the third digital scan,
   wherein locating the condylar axis is based on at least the first, second and third digital scans and the first, second and third bite digital data sets.

3. A method as in claim 1, wherein acquiring the digital scans comprises acquiring at least one of a digitized X-ray, a computed tomography scan and a magnetic resonance imaging scan.

4. A method as in claim 1, wherein the digital scans are acquired while the patient is biting a registration device that contacts only anterior teeth of the patient.

5. A method as in claim 1, wherein the digital scans are acquired while the patient is biting a registration device that contacts only posterior teeth of the patient.

6. A method as in claim 1, further comprising providing at least one image showing the patient's bite configuration.

7. A method as in claim 6, further comprising providing a series of images showing articulation of a lower jaw of the patient about the condylar axis.

8. A method as in claim 7, wherein the series of images is generated automatically via a computer algorithm.

9. A method as in claim 6, further comprising manipulating the at least one image to show an alternative bite configuration for the patient.

* * * * *